(12) United States Patent
Pilgrim et al.

(10) Patent No.: US 8,071,723 B2
(45) Date of Patent: Dec. 6, 2011

(54) STABLE D-DIMER LIQUID PREPARATION

(75) Inventors: Sabine Pilgrim, Marburg (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 188 days.

(21) Appl. No.: 12/153,956

(22) Filed: May 28, 2008

(65) Prior Publication Data
US 2009/0011520 A1    Jan. 8, 2009

(30) Foreign Application Priority Data
Jun. 4, 2007   (DE) .................. 10 2007 026 153

(51) Int. Cl.
*A61K 35/14*    (2006.01)
(52) U.S. Cl. ......................... 530/382; 436/15
(58) Field of Classification Search ................ 530/382; 435/13, 967; 436/15
See application file for complete search history.

(56) References Cited

U.S. PATENT DOCUMENTS
6,132,719 A    10/2000  Kohno
6,432,657 B1    8/2002  Kikuchi FOREIGN PATENT DOCUMENTS
| EP | 0 413 587 | | 2/1991 |
|---|---|---|---|
| EP | 1 695 984 | A1 | 8/2006 |
| EP | 1695984 | A1 | 8/2006 |
| WO | WO 02/39114 | A2 | 5/2002 |
| WO | WO 0239114 | A2 | 5/2002 |
| WO | WO 2007/089665 | A2 | 8/2007 |
| WO | WO 2007089665 | A2 | 8/2007 |

OTHER PUBLICATIONS

Whitaker, A.N. et al., "Measurement of cross linked fibrin derivatives in plasma: an immunoassay using monoclonal antibodies," J. Clin. Pathol. 37: 882-7 (1984).

Dempfle, "D-dimer testing and venous thromboembolism: four view points," *J. of Thrombosis and Haemostasis*, 3: 377-379 (2005).

Edlund, "A proposed stoichiometrical calibration procedure to achieve transferability of D-dimer measurements and to characterize the performance of different methods," *Clinical Biochemistry*, 39: 137-142 (2006).

*Primary Examiner* — Ralph Gitomer
(74) *Attorney, Agent, or Firm* — Finnegan, Henderson, Farabow, Garrett & Dunner, L.L.P.

(57) ABSTRACT

The invention is in the field of coagulation diagnosis and relates to a liquid, buffer-based D-dimer composition, which additionally contains fibrinogen and which is suitable as a standard material for control or calibration purposes for D-dimer test procedures.

17 Claims, 2 Drawing Sheets

STABLE D-DIMER LIQUID PREPARATION

This application claims priority to German Application No. 10 2007 026 153.7, filed Jun. 4, 2007, which is incorporated by reference in its entirety.

The invention is in the field of coagulation diagnosis and relates to a liquid preparation consisting of a D-dimer-containing buffer, which is suitable as a standard material for control or calibration purposes.

D-dimer is an important laboratory parameter for the detection of coagulation activation. The aim of coagulation is the formation of a blood clot (thrombus), which in the case of injury should keep the blood loss as low as possible by the closure of the wound. The conversion of fibrinogen occurring ubiquitously in the blood to insoluble fibrin is an essential constituent of blood clot formation. The fibrin precursor fibrinogen is a large molecular weight, dimeric glycoprotein, which consists of three pairs of chains ($\alpha$, $\beta$, and $\gamma$ chains), which are linked by disulfide bonds. Fibrin formation takes place by a sequence of enzymatic, proteolytic processes. First, thrombin cleaves fibrinopeptide A from the N-terminal regions of the $\alpha$ chains and then fibrinopeptide B from the $\beta$ chains of fibrinogen, whereby DesAABB-fibrin results in monomer form. These soluble fibrin monomers polymerize spontaneously to give long fibers and finally to give a densely branched network, this form of fibrin still being soluble. This still relatively unstable fibrin is finally stabilized by the activity of coagulation factor XIIIa (F XIIIa) by F XIIIa first crosslinking the $\gamma$ chains of fibrin to give dimers and finally the $\alpha$ chains to give polymers. A system which acts as an antagonist of the coagulation system is the fibrinolysis system, whose object it is to redissolve fibrin clots and thus, for example, to guarantee the recanalization of the blood vessel. During fibrinolysis, both fibrinogen and fibrin are proteolytically cleaved by plasmin, various cleavage products, which are now water-soluble again, resulting. The degradation products of fibrinogen and fibrin differ. The smallest fibrin-specific degradation product is the D-dimer, which consists of D domains covalently bonded by F XIIIa. D-dimer is therefore suitable as a marker of fibrinolysis and is an important diagnostic parameter for the detection of the coagulation activation. Antibodies which specifically recognize D-dimers are therefore employed in the diagnosis of the intravascular coagulation activation. The quantitative determination of the D-dimer antigen in plasma or serum samples gives information for the exclusion of venous thrombosis and pulmonary embolism and is used for the diagnosis of disseminated intravascular coagulation.

Various test procedures for the quantitative detection of D-dimer in human plasma or serum samples are known. D-dimer-specific antibodies make possible both the use of immunochemical procedures such as latex agglutination assays or of enzyme immunoassays. In the various D-dimer test procedures, it is customary to employ D-dimer-containing preparations of very different D-dimer antigen concentration as controls or calibrators, controls for the normal measuring range customarily containing less than 0.5 mg/l FEU D-dimer and controls for the pathological measuring range containing more than 0.5 mg/l FEU D-dimer. FEU denotes fibrinogen equivalent unit and is the most customary unit used worldwide for D-dimer. 2 mg/l FEU D-dimer here correspond to 1 mg/l of D-dimer, the conversion being based on the fact that two D-dimer molecules result from one fibrinogen molecule after fibrin formation and subsequent fibrinolysis.

The D-dimer controls or calibrators for the quality control of commercial D-dimer tests customarily consist of a plasma matrix and are in the main prepared from stabilized, human plasma, to which defined amounts of D-dimer are added. As is known, D-dimer, for example, can be obtained by treating human plasma with a coagulation activator and subsequently with plasmin, whereby first fibrin formation and subsequently fibrin degradation are induced. The D-dimers formed in this so-called "clot lysis" plasma by fibrin degradation can be enriched and purified. Alternatively, for the obtainment of D-dimer pure fibrinogen can also be polymerized by addition of calcium chloride, F XIIIa and thrombin to give fibrin, which can subsequently be degraded by incubation with plasmin.

The majority of these known controls or calibrators are at present lyophilized for stability reasons after filling. In principle, however, it is also possible to prepare liquid, non-lyophilized D-dimer controls or calibrators with adequate shelf life. Bio-Rad Laboratories supplies, for example, liquid D-dimer controls based on human plasma (LIQUICHEK™ D-dimer control, level 1, 2 and 3), whose lifespans are stated as three years. Another liquid D-dimer-containing product, in which D-dimer was present in a stabilized buffer, had a lifespan of 18 months. Stabilization was carried out here by means of general, nonspecific stabilizers such as bovine albumin and aprotinin as an inhibitor of serine proteases such as thrombin or plasmin. D-dimer-specific stabilizers or procedures which are suitable for the stabilization of the analyte in a liquid are not known, however.

The object on which the invention was based thus also consisted in providing a composition which contains D-dimer and which has an adequate shelf life in the liquid state, i.e. guarantees a constant recovery of the analyte D-dimer.

The object is achieved by the provision of a composition as claimed in claim 1.

The invention relates to a composition comprising a buffer which contains D-dimer and additionally fibrinogen. It has been found that by the addition of fibrinogen to D-dimer, compositions are obtained with an adequately constant recovery of D-dimer even at a storage temperature of 37° C. for up to 24 weeks. In contrast, it is not possible to recover adequately constant D-dimer from compositions to which no fibrinogen is added even when stored at 37° C. for as little as 10 weeks.

The composition according to the invention comprises a buffer and is thus distinct from preparations which comprise a plasma matrix. Preparations based on a plasma matrix, which are used as calibrators or controls, customarily consist of normal or deficient plasma and accordingly contain endogenous fibrinogen. A composition according to the invention based on a buffer comprises a buffered solution which contains no endogenous fibrinogen and to which the analyte D-dimer and fibrinogen are added in purified or partially purified form. For the preparation of the buffer, substances are especially suitable which have a buffering effect in the pH range from about 5 to about 10. Suitable substances are, for example, phosphate buffer, acetate buffer, citrate buffer, arginine buffer, histidine buffer and TRIS buffer. A particularly preferred buffer is one having a pH of about 6 to about 9.

The composition according to the invention comprising a buffer contains D-dimer in the desired purity and concentration. Preferentially, the D-dimer contained in the composition is D-dimer from human clot lysis plasma or a degradation product of pure, preferably human, fibrinogen which has been polymerized to give fibrin, for example, by addition of calcium chloride, F XIIIa and thrombin and subsequently degraded by incubation with plasmin, urokinase or elastase or a combination thereof. The purification or enrichment of D-dimer can be carried out by any desired procedure suitable to the person skilled in the art. Depending on the desired purity of the D-dimer, purification procedures can be used to separate impurities such as carbohydrates, lipids, nucleic acids, proteins, and/or other biomolecules from the D-dimer. Examples of procedures which, as is known, are used for the purification of proteins, are chromatographic separation procedures, such as ion exchange, gel filtration, hydrophobic interaction, or affinity chromatography. In addition, preparative gel electrophoresis, preparative isoelectric focusing, chromatofocusing, precipitation and ultracentrifugation can also be used for the purification of proteins from a protein mixture. Preferentially, a composition according to the invention contains D-dimer in a final concentration of about 0.1 to about 100 mg/l of FEU D-dimer.

The addition of D-dimer to the buffer can also be carried out, for example, by mixing a D-dimer-containing clot lysis plasma with an aqueous, buffered solution without further purification or enrichment of D-dimer. On account of the treatment of the starting plasma with an excess of coagulation activator and the fibrin formation thereby achieved, clot lysis plasma should no longer contain any endogenous fibrinogen. In practice, however, it is not to be excluded that traces of endogenous fibrinogen which—if they are detectable at all—do not have any decisive influence on the stability of a composition according to the invention, can be present in a clot lysis plasma. Preferentially, the D-dimer concentration of the clot lysis plasma is determined before mixing, and the clot lysis plasma is diluted with the aqueous, buffered solution such that the desired D-dimer concentration is achieved in the resulting buffer. The resulting buffer, however, should contain not more than about 10 percent by volume of clot lysis plasma. The invention accordingly relates to compositions which comprise a buffer which comprises about 0 to about 10 percent by volume of clot lysis plasma. Compositions according to the invention are to be preferred which comprise a buffer which contains at most about 5 percent by volume, particularly preferably at most about 1 percent by volume, particularly preferably at most about 0.5 percent by volume of clot lysis plasma.

Furthermore, the fibrinogen of the compositions of the invention may be of human, animal (e.g. from cattle, horse, cat, dog, rabbit), or recombinant origin. Preferentially, the fibrinogen is purified fibrinogen, which is also commercially obtainable. Pure fibrinogen can be obtained by any desired procedure suitable to the person skilled in the art, including the purification of fibrinogen from an organic raw material, in which fibrinogen occurs naturally or was produced by recombinant DNA technology. Depending on the desired purity of the fibrinogen, purification procedures can be used to separate impurities such as carbohydrates, lipids, nucleic acids, proteins, and/or other biomolecules from the fibrinogen. Raw materials for obtaining fibrinogen can be, for example, animal or human tissue or body fluids (e.g. blood, plasma), supernatants or lysates of animal or human cell cultures, or cultures of eukaryotic cells or of microorganisms, such as bacteria or fungi, which express recombinant fibrinogen. Examples of procedures which, as is known, are used for the purification of proteins are chromatographic separation procedures, such as ion exchange, gel filtration, hydrophobic interaction or affinity chromatography. In addition, preparative gel electrophoresis, preparative isoelectric focusing, chromatofocusing, precipitation and ultrafiltration can also be used for the purification of proteins from a protein mixture. Preferentially, compositions according to the invention comprise fibrinogen in a final concentration of more than about 0.025 g/l and at most about 2.5 g/l, preferably of about 0.1 g/l to about 1 g/l, and particularly preferably of about 0.2 g/l to about 0.5 g/l.

Preferentially, the composition according to the invention can contain additional substances for stabilization, such as, for example, antioxidants or reducing agents for the prevention of oxidative degradation, proteinase inhibitors for the prevention of proteolytic processes, particularly preferably aprotinin, chelating agents for the exclusion of heavy metal ions or bacteriostatics and fungicides for the avoidance of microbial growth, particularly preferably sodium azide. Activity losses due to physical effects such as adsorption, denaturation by surfaces, heat denaturation, drying, repeated freezing and thawing can be reduced, for example, by addition of glycerol, carbohydrates, amino acids, hydrophilic polymers or inert proteins, such as human serum albumin (HSA), bovine serum albumin (BSA) or ovalbumin. Furthermore, a composition according to the invention can also contain so-called volume replacements, such as, for example, polygeline (HAEMACCEL®).

Even if a particular advantage of a composition according to the invention is that it is particularly stable in liquid form, it is, however, also possible to lyophilize the composition for storage purposes.

A further subject of the present invention is the use of a composition according to the invention as a control or calibrator in a test procedure, in particular in an immunochemical test procedure for the quantitative determination of D-dimer in human serum or plasma samples. Particularly preferably, a composition according to the invention is used for the control or calibration of a D-dimer test procedure in which the D-dimer antigen is detected by means of an antibody. In particular, the monoclonal antibody 8D3 is used. For antibody 8D3 see: Holvoet, P. et al. (1989) "Binding properties of monoclonal antibodies against human fragment D-dimer of cross-linked fibrin to human plasma clots in an in vivo model in rabbits." Thrombosis and Haemostasis 61 (2): 307-313. Preferentially, for this procedure a number of compositions of different D-dimer concentrations are prepared and measured to generate a standard curve of D-dimer concentration. The standard curve could be used, for example, to differentiate normal (<0.5 mg/l FEU) and pathologically high (>0.5 mg/l FEU) D-dimer levels.

The present invention furthermore relates to a procedure for the production of a composition according to the invention which contains D-dimer. In the process according to the invention, a composition comprising D-dimer is mixed with a fibrinogen solution in a liquid buffer, e.g. purified D-dimer from human clot lysis plasma dissolved in a buffer. In a particularly preferred embodiment, the composition is incubated for a limited period at about 30 to about 50° C. after mixing. Particularly preferably, the incubation is carried out at about 37° C. This incubation step causes a stabilization of the D-dimer liquid composition. Preferentially, this incubation is carried out for a period of 4 hours up to 7 days, particularly preferably for 12 hours up to 3 days, before the composition is stored at the desired storage temperature (customarily in a refrigerator at 2 to 8° C.) for a number of months until further use.

The examples described below serve for the exemplary illumination of individual aspects of this invention and are not to be understood as a restriction:

EXAMPLES

Example 1

Production of a D-Dimer Composition According to the Invention on a Small Scale

For the obtainment of D-dimer, clot lysis plasma was prepared from normal human plasma by addition of thrombin and subsequent addition of urokinase. The clot lysis plasma prepared in this way contained 1193 mg/l of FEU D-dimer and was used as a D-dimer composition for the production of the following compositions based on a buffer:

| Formulation 1: | 3 mg/l FEU D-dimer |
| | 50 mM NaH$_2$PO$_4$ |
| | 10 g/l of bovine serum albumin |
| | 0.1% (v/v) Tween ® 20 |
| | 80 000 KIU/l of aprotinin |
| | 0.04% (w/v) sodium azide |
| | pH 6.9 |
| Formulation 2: | 3 mg/l FEU D-dimer |
| | 50 mM NaH$_2$PO$_4$ |
| | 10 g/l of bovine serum albumin |
| | 0.1% (v/v) Tween ® 20 |
| | 80 000 KIU/l of aprotinin |
| | 0.04% (w/v) sodium azide |
| | 0.25 g/l of human, clottable fibrinogen |
| | (Sigma-Aldrich, catalogue no.: F4883) |
| | pH 6.9 |

The two formulations each with a total volume of 0.15 l differ only in that the formulation 2 according to the invention additionally contained 0.25 g/l of human fibrinogen.

Figure 1:
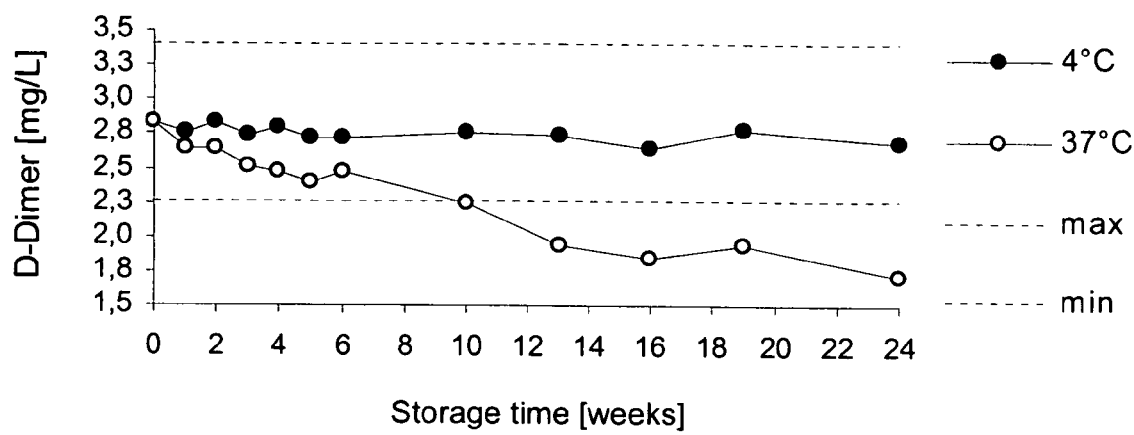
FIG. 1 Shelf life of D-dimer in liquid buffer without fibrinogen at different storage temperatures (max, min: tolerance limits).
Figure 2:
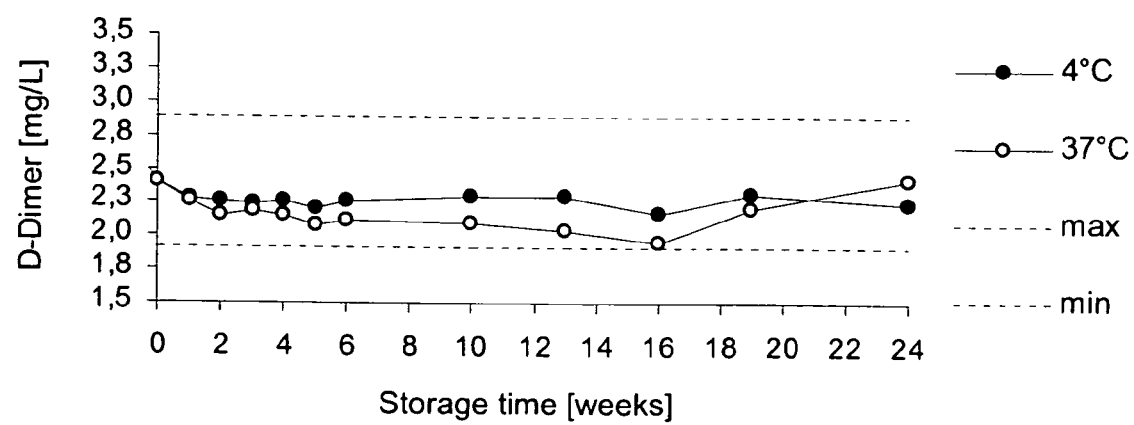
FIG. 2 Shelf life of D-dimer in a composition according to the invention in a liquid buffer with 0.25 g/l of fibrinogen at different storage temperatures (max, min: tolerance limits).

Both compositions were filled into glass vessels after mixing the components at room temperature and were incubated for 3 days at 37° C. Subsequently, the compositions were stored at 2 to 8° C. (desired storage temperature) or at 37° C. (for the generation of accelerated shelf life data). After appropriate storage periods, the D-dimer concentration was determined in a coagulation analyzer (BCS® system, Dade Behring Marburg GmbH, Marburg, Germany) using a latex particle-enhanced immunoturbidimetric test which was based on the principle of latex agglutination by the D-dimer-specific antibody 8D3 (INNOVANCE® D-dimer test, Dade Behring Marburg GmbH, Marburg, Germany). The results are shown in FIGS. 1 and 2 (FIG. 1: D-dimer in liquid buffer without fibrinogen (formulation 1); FIG. 2: D-dimer in liquid buffer with fibrinogen (formulation 2).

The shelf life studies unequivocally show that the fibrinogen-containing D-dimer composition exhibits a constant recovery of its D-dimer concentration during a storage period of 24 weeks at 37° C. if the tolerance range drawn in between the tolerance limits (max, min) is defined as an acceptance criterion. The respective tolerance range (+/−20%) was defined by means of the D-dimer concentration recovered after preincubation at time 0. In contrast to this, the D-dimer composition without fibrinogen (FIG. 1) falls short of the tolerance range for an acceptable shelf life after a storage time of 10 weeks at 37° C. This shows that fibrinogen prolongs the shelf life of D-dimer in buffer.

Example 2

Production of D-Dimer Compositions on a Large Scale with and without Preincubation at +37° C.

Figure 3:
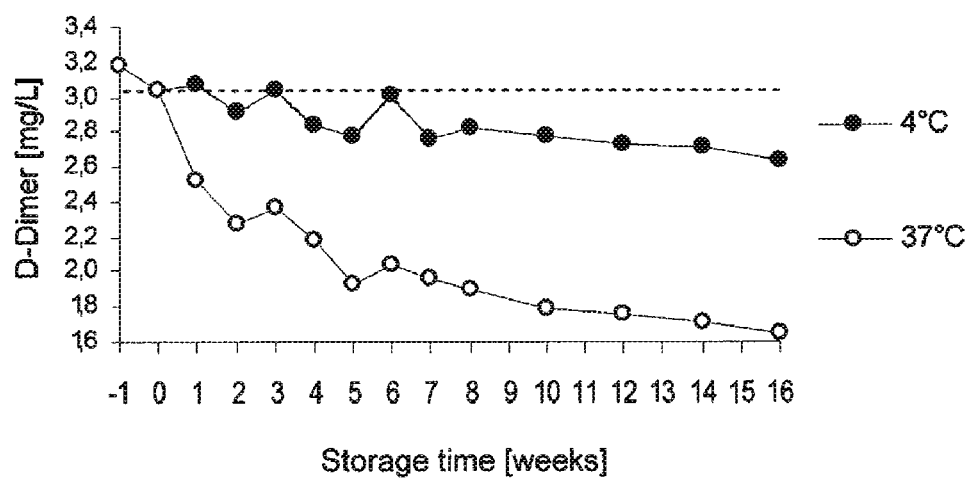
FIG. 3 Shelf life of D-dimer in a composition according to the invention in liquid buffer with 0.25 g/l of fibrinogen without preincubation at 37° C. for 1 week (from −1 to 0), but incubation at 2° C. to 8° C., at subsequently different storage temperatures. The timepoint "−1 week" corresponds to the timepoint of composition and of desired value determination (desired value=dashed line).

In order to investigate the effect of preincubation of the composition according to the invention at +37° C., 10 l of a fibrinogen-containing D-dimer composition according to formulation 2 (see Example 1) were prepared. A part of this composition was stored at +2 to +8° C. for one week after mixing the components at room temperature. In parallel to this, another part of this composition was stored (preincubated) at +37° C. for one week. Subsequently, in each case a part of the two batches was stored at +2 to +8° C. (desired storage temperature) or at +37° C. (for the generation of accelerated shelf life data). After appropriate storage periods, the D-dimer concentration was determined (see Example 1). The results are shown in FIGS. 3 and 4.

Figure 4:
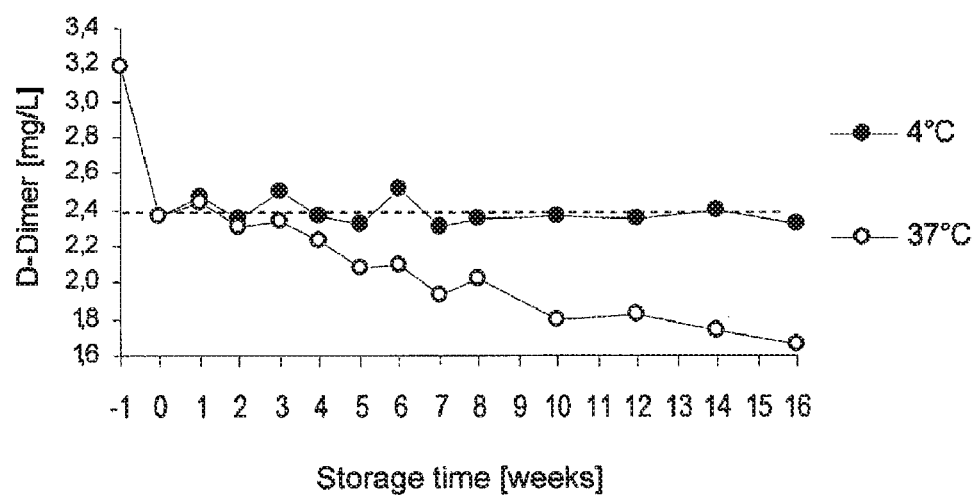
FIG. 4 Shelf life of D-dimer in a composition according to the invention in liquid buffer with 0.25 g/l of fibrinogen with preincubation at 37° C. for 1 week (from −1 to 0) at subsequently different storage temperatures. The timepoint "−1 week" corresponds to the timepoint of the composition and of the desired value determination (desired value=dashed line).

The results show that after preincubation of the fibrinogen-containing D-dimer composition in buffer at +37° C. the D-dimer concentration was indeed lower than at the time of composition, but that after preincubation the D-dimer concentration only decreases by 30% at +37° C. and by 2% at 4° C. after a period of 16 weeks in comparison to the starting value (0 weeks) (FIG. 4). For the same composition which was not preincubated, however, the D-dimer concentration decreased by 54% after a period of 16 weeks at +37° C. and by 14% at 4° C. (FIG. 3). A preincubation step at +37° C. accordingly prolongs the shelf life of fibrinogen-containing D-dimer composition in a clearly measurable manner.

The invention claimed is:

1. A stable D-dimer composition comprising a mixture comprising a buffer, D-dimer, and fibrinogen, wherein the stable D-dimer composition comprises fibrinogen in a concentration of more than about 0.025 g/l to at most about 2.5 g/l, and wherein the stable D-dimer composition is obtained by incubating said mixture at about 30° C. to about 50° C.

2. The stable D-dimer composition of claim 1, wherein the fibrinogen is human or animal fibrinogen.

3. The stable D-dimer composition of claim 1, wherein the fibrinogen concentration is about 0.1 g/l to about 1 g/l.

4. The stable D-dimer composition of claim 1, wherein the fibrinogen concentration is about 0.2 g/l to about 0.5 g/l.

5. The stable D-dimer composition of claim 1, wherein the composition is liquid.

6. The stable D-dimer composition of claim 1, wherein the composition comprises about 0.1 to about 100 mg/l fibrinogen equivalent unit (FEU) D-dimer.

7. The stable D-dimer composition of claim 1, which additionally comprises an inert protein, and/or a protease inhibitor and/or a detergent and/or an additive having bactericidal and/or fungicidal action.

8. The stable D-dimer composition of claim 7, wherein the inert protein comprises bovine serum albumin.

9. The stable D-dimer composition of claim 7, wherein the additive having bactericidal and/or fungicidal action comprises sodium azide.

10. The stable D-dimer composition of claim 1, wherein the composition comprises about 0 to at most about 10 percent by volume of clot lysis plasma.

11. The stable D-dimer composition of claim 10, wherein the buffer comprises at most about 5 percent by volume of clot lysis plasma.

12. The stable D-dimer composition of claim 11, wherein the buffer comprises at most about 1 percent by volume of clot lysis plasma.

13. The stable D-dimer composition of claim 12, wherein the buffer comprises at most about 0.5 percent by volume of clot lysis plasma.

14. The stable D-dimer composition claim 1, wherein the mixture is incubated at about 37° C.

15. The stable D-dimer composition claim 1, wherein the mixture is incubated at about 30° C. to about 50° C. for 4 hours to 7 days.

16. The stable D-dimer composition claim 15, wherein the mixture is incubated for 12 hours to 3 days.

17. The stable D-dimer composition claim 1, wherein the stable D-dimer composition is a D-dimer calibrator and/or control composition.

* * * * *